United States Patent [19] [11] Patent Number: 4,753,930
Maurer et al. [45] Date of Patent: Jun. 28, 1988

[54] INSECTICIDAL AND NEMATICIDAL PYRIMIDINYL-THIONOPHOSPHORIC ACID ESTERS

[75] Inventors: Fritz Maurer, Wuppertal; Benedikt Becker, Mettmann; Bernhard Homeyer, Leverkusen, all of Fed. Rep. of Germany

[73] Assignee: Bayer Aktiengesellschaft, Leverkusen, Fed. Rep. of Germany

[21] Appl. No.: 13,609

[22] Filed: Feb. 12, 1987

Related U.S. Application Data

[63] Continuation of Ser. No. 754,047, Jul. 11, 1985, abandoned.

[30] Foreign Application Priority Data

Jul. 14, 1984 [DE] Fed. Rep. of Germany ....... 3426007

[51] Int. Cl.$^4$ .......................... A01N 57/16; C07F 9/65
[52] U.S. Cl. ........................................ 514/87; 544/243
[58] Field of Search ........................... 544/243; 514/87

[56] References Cited

U.S. PATENT DOCUMENTS 3,823,235 7/1974 Haubein ................. 514/87
3,981,993 9/1976 Maurer et al. ......... 514/87
4,014,996 3/1977 Maurer et al. ......... 514/87
4,053,594 10/1977 Riebel et al. .......... 514/87
4,093,718 6/1978 Maurer et al. ......... 514/87
4,113,860 9/1978 Maurer et al. ......... 514/87
4,233,294 11/1980 Maurer et al. ......... 514/87

FOREIGN PATENT DOCUMENTS 2415058 10/1975 Fed. Rep. of Germany .
2507702 9/1976 Fed. Rep. of Germany .
3426007 1/1986 Fed. Rep. of Germany ...... 544/243

Primary Examiner—Nicholas S. Rizzo
Assistant Examiner—Diana G. Rivers
Attorney, Agent, or Firm—Sprung Horn Kramer & Woods

[57] ABSTRACT

Novel insecticides and nematicides of the formula

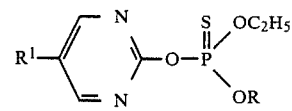

in which
R is i-propyl or sec.-butyl, and
$R^1$ is hydrogen or halogen.

10 Claims, No Drawings

INSECTICIDAL AND NEMATICIDAL PYRIMIDINYL-THIONOPHOSPHORIC ACID ESTERS

This is a continuation, of application Ser. No. 754,047 filed July 11, 1985 abandoned.

The invention relates to new pyrimidin-2-yl-thionophosphoric acid esters, a process for their preparation and their use in agents for combating pests, in particular as insecticides and nematicides.

It is known that certain thionophosphoric acid esters and ester-amides, such as, for example, 0,0-diethyl 0-(pyrimidin-2-yl), 0-ethyl 0-n-propyl 0-(pyrimidin-2-yl) and 0-ethyl-0-n-propyl-0-5-bromo-pyrimidin-2-yl) thionophosphates, have an insecticidal action (compare U.S. Pat. No. 3,981,993, issued Sept. 21, 1976, corresponding to DE-OS German Published Specification No. 2,415,058, U.S. Pat. No. 4,093,718, issued June 6, 1978, corresponding to DE-OS German Published Specification No. 2,507,702, U.S. Pat. No. 3,741,968 and Swiss Patent Specification No. 546,259).

However, the action and duration of action of these compounds are not always completely satisfactory, especially in certain insects.

New pyrimidin-2-yl-thionophosphoric acid esters of the formula (I)

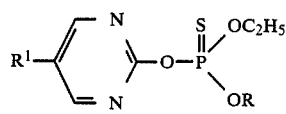

in which
R represents i-propyl or sec.-butyl and
$R^1$ represents hydrogen or halogen, have now been found.

It has furthermore been found that the new pyrimidin-2-yl-thionophosphoric acid esters of the formula (I) are obtained by a process in which 2-hydroxypyrimidines of the formula (II)

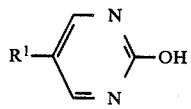

in which $R^1$ has the abovementioned meaning, or the corresponding alkali metal, alkaline earth metal or ammonium salts, are reacted with halides of the formula (III)

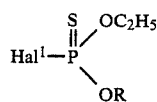

in which
R has the abovementioned meaning and
Hal1 represents halogen, such as chlorine or bromine, if appropriate in the presence of an acid acceptor and if appropriate in the presence of a diluent.

The new pyrimidin-2-yl-thionophosphoric acid esters of the formula (I) are distinguished in an outstanding manner by a particularly high and long activity as agents for combating pests, in particular as insecticides and nematicides.

The invention preferably relates to compounds of the formula (I) in which
R represents i-propyl or sec.-butyl and
$R^1$ represents hydrogen, fluorine, chlorine or bromine.

Particularly preferred compounds of the formula (I) are those in which
R represents i-propyl or sec.-butyl and
$R^1$ represents hydrogen, fluorine or bromine.

If, for example, 0-ethyl 0-i-propyl thionophosphoric acid diester-chloride and 2-hydroxy-pyrimidine are used as starting substances for the process according to the invention, the corresponding reaction can be outlined by the following equation:

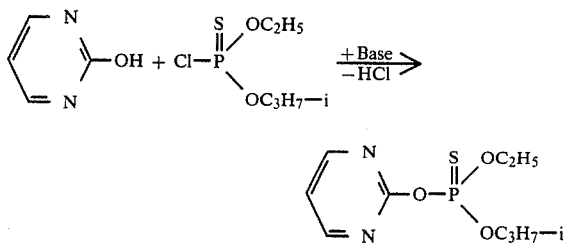

Formula (II) provides a definition of the 2-hydroxypyrimidines and the corresponding alkali metal, alkaline earth metal or ammonium salts to be used as starting substances in the process according to the invention for the preparation of the new compounds of the formula (I). In this formula (II), $R^1$ represents those radicals which have been mentioned above in the definition for formula (I). The sodium, potassium or calcium salts are preferably employed as the alkali metal or alkaline earth metal salts.

The compounds of the formula (II) are known and/or can be prepared by generally known processes and methods (compare, for example, DE-OS (German Published Specification No.) 2,507,702 and U.S. Pat. No. 3,741,968).

Examples which may be mentioned of the compounds of the formula (II) are: 2-hydroxy-pyrimidine, 5-fluoro-, 5-chloro- and 5-bromo-2-hydroxypyrimidine and the corresponding sodium, potassium, calcium and ammonium salts.

Formula (III) provides a definition of the halides also to be used as starting substances. In this formula, R represents those radicals which have been mentioned in the definition for formula (I). Hal1 in this formula (III) represents halogen, such as, in particular, chlorine or bromine.

The compounds of the formula (III) are known.

Examples which may be mentioned of the halides of the formula (III) are: 0-ethyl 0-i-propyl and 0-ethyl 0-sec.-butyl thionophosphoric acid ester-chloride and -bromide.

The process according to the invention for the preparation of the new pyrimidin-2-yl-thionophosphoric acid esters of the formula (I) is preferably carried out using diluents. Possible diluents are virtually all the inert organic solvents.

These include, in particular, aliphatic and aromatic, optionally halogenated hydrocarbons, such as pentane, hexane, heptane, cyclohexane, petroleum ether, gasoline, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylene sulphone and hexamethylphosphoric acid triamide.

If appropriate, the process can be carried out in the presence of acid acceptors. Acid acceptors which can be used are all the customary acid-binding agents. Agents which have proved particularly suitable are alkali metal carbonates and alcoholates, such as sodium carbonate, potassium carbonate, sodium methylate or ethylate and potassium methylate or ethylate, alkali metal hydrides, such as sodium hydride, and furthermore aliphatic, aromatic or heterocyclic amines, for example triethylamine, trimethylamine, dimethylaniline, dimethylbenzylamine and pyridine.

The process according to the invention is in general carried out at temperatures between 0° C. and 100° C. The range between 20° C. and 80° C. is preferred. The reactions are in general carried out under normal pressure.

For carrying out the process according to the invention, the starting substances are usually employed in approximately equimolar amounts. An excess of either of the reaction components provides no substantial advantages. The reaction is in general carried out in a suitable diluent in the presence of an acid acceptor and the reaction mixture is stirred at the required temperature for several hours. An organic solvent, for example toluene, is then added and the organic phase is worked up in the customary manner by washing, drying and distilling off the solvent.

The new compounds are obtained in the form of oils, some of which cannot be distilled without decomposition, but can be purified from the last volatile constituents by so-called "incipient distillation", that is to say by prolonged heating to moderately elevated temperatures under reduced pressure, and can in this way be purified. They are characterized by their refractive index.

The active compounds are well tolerated by plants, and are suitable for combating animal pests, especially insects and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attegenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp.. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinelle frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.. From the order of the Arachnida, for example, *Scorpio maurus* and *Latrodectus mactans.*

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds of the formula (I) according to the invention are distinguished by an outstanding insecticidal and nematicidal activity. When used against soil insects in particular, they exhibit an outstanding action and a particularly long activity against beetle larvae, such as, for example, *Phaedon cochleariae*, and aphids, such as, for example, *Myzus persicae*.

The new compounds are thus particularly well suitable for use for long-lasting combating of soil insects and nematodes.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms and others.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

EXAMPLE A

Laphygma test
Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Laphygma frugiperda*), as long as the leaves are still moist.

After the specified period of time, the destruction in % is determined. 100% means that all the caterpillars have been killed; 0% means that none of the caterpillars have been killed.

In this test, for example, the compounds from preparation Examples (1) and (2) showed a destruction of 100% after 3 days, at an active compound concentration of 0.01%.

EXAMPLE B

Test nematode: *Meloidogyne incognita*
Solvent: 3 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, potatoes are planted in and the pots are kept at a greenhouse temperature of 18° C.

After six weeks, the potato roots are examined for cysts and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compounds from preparation Examples (1) and (2) showed a destruction of 100%, at an active compound concentration of 20 ppm.

EXAMPLE C

Test insect: *Phaedon cochleariae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all the test animals have been killed and 0% if just as many test insects are still alive as in the case of the untreated control.

In this test, for example, the compounds from preparation Examples (I) and (2) showed a destruction of 100%, at an active compound concentration of 5 ppm.

EXAMPLE D

Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

In this test, for example, the compounds from preparation Examples (1) and (2) showed a destruction of 100%, at an active compound concentration of 5 ppm.

EXAMPLE E

Test insect: *Phorbia antiqua* maggots (in the soil)
Solvent: 3 parts by weight of acetone
Emulsifer: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with the soil. The concentration of the active compound in the preparation is of practically no importance, only the amount by weight of active compound per unit volume of soil, which is given in ppm (=mg/l) being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds from preparation Examples (1) and (2) showed a destruction of 100% at an active compound concentration of 5 ppm.

PREPARATION EXAMPLES

EXAMPLE 1

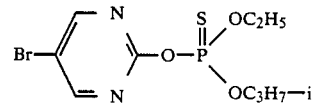

A mixture of 17.5 g (0.1 mole) of 2-hydroxy-5-bromopyrimidine (for the preparation, compare DE-OS (German Published Specification) No. 2,507,702), 20.7 g (0.15 mole) of potassium carbonate, 20.2 g (0.1 mole) of 0-ethyl 0-i-propyl-thionophosphoric acid diester-chloride and 300 ml of acetonitrile is stirred at 50° C. for 23 hours. It is then cooled to 20° C., 400 ml of toluene are added and the mixture is shaken twice with 200 ml of water each time. The organic phase is separated off, dried over sodium sulphate and evaporated in vacuo. After incipient distillation at 80° C. under a high vacuum, 12.8 g (38% of theory) of O-ethyl O-i-propyl O-(5-bromo-pyrimidin-2-yl) thionophosphate remain in the form of a light brown oil with a refractive index $n_D^{20}$: of 1.5182.

The following compounds of the formula (I) can be prepared analogously to Example 1:

TABLE 1

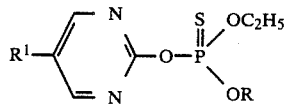
(I)

| Example No. | R | $R^1$ | Refractive index |
|---|---|---|---|
| 2 | $C_3H_7$—i | H | $n_D^{21}$: 1.5028 |
| 3 | $C_4H_9$—sec. | Br | $n_D^{20}$: 1.5159 |
| 4 | $C_3H_7$—i | Cl | |
| 5 | $C_4H_9$—sec. | H | $n_D^{20}$: 1.4956 |
| 6 | $C_4H_9$—sec. | Cl | |
| 7 | $C_3H_7$—i | F | $n_D^{23}$: 1.4919 |
| 8 | $C_4H_9$—sec. | F | |

It will be understood that the specification and examples are illustrative but not limitative of the present invention and that other embodiments within the spirit and scope of the invention will suggest themselves to those skilled in the art.

We claim:

1. A compound of the formula

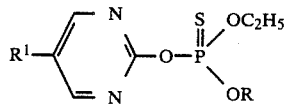

in which
R is i-propyl or sec.-butyl, and
$R^1$ is hydrogen or halogen.

2. A compound according to claim 1, in which $R^1$ is hydrogen, fluorine, chlorine or bromine.

3. A compound according to claim 1, in which $R^1$ is hydrogen, fluorine or bromine.

4. A compound according to claim 1, wherein such compound is O-ethyl O-i-propyl O-(5-bromo-pyrimidin-2-yl) thionophosphate of the formula

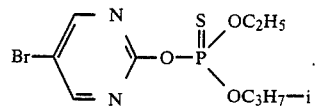

5. A compound according to claim 1, wherein such compound is O-ethyl O-i-propyl O-pyrimidin-2-yl thionophosphate of the formula

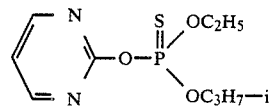

6. An insecticidal and nematicidal composition comprising an insecticidally and nematicidally effective amount of a compound according to claim 1 in admixture with a diluent.

7. A method of combating insects and nematodes which comprises applying to an insect, nematode or an insect or nematode habitat an insecticidally or nematicidally effective amount of a compound according to claim 1.

8. A method of combating insects and nematodes which comprises applying to an insect, nematode or an insect or nematode habitat an insecticidally or nematicidally effective amount of a compound according to claim 4.

9. A method of combating insects and nematodes which comprises applying to an insect, nematode or an insect or nematode habitat an insecticidally or nematicidally effective amount of a compound according to claim 5.

10. A compound according to claim 1, in which $R^1$ is halogen.

* * * * *